United States Patent
Desrochers et al.

(10) Patent No.: US 7,415,901 B2
(45) Date of Patent: Aug. 26, 2008

(54) DUCT PROBE ASSEMBLY SYSTEM FOR MULTIPOINT AIR SAMPLING

(75) Inventors: Eric M. Desrochers, Millis, MA (US); Gordon P. Sharp, Newton, MA (US)

(73) Assignee: Aircuity, Inc., Newton, MA (US)

( * ) Notice: Subject to any disclaimer, the term of this patent is extended or adjusted under 35 U.S.C. 154(b) by 0 days.

(21) Appl. No.: 11/755,040

(22) Filed: May 30, 2007

(65) Prior Publication Data

US 2007/0240490 A1 Oct. 18, 2007

Related U.S. Application Data

(62) Division of application No. 11/312,164, filed on Dec. 20, 2005.

(51) Int. Cl.
*G01N 1/24* (2006.01)
(52) U.S. Cl. .................... 73/863.3; 236/1 B
(58) Field of Classification Search .......... None
See application file for complete search history.

(56) References Cited

U.S. PATENT DOCUMENTS

| 2,322,018 | A | * | 6/1943 | Huber ................. 73/202 |
| 2,475,857 | A | * | 7/1949 | Reinert ................ 73/863.12 |
| 4,547,079 | A | | 10/1985 | Alamprese et al. |
| 5,292,280 | A | | 3/1994 | Janu et al. |
| 6,125,710 | A | | 10/2000 | Sharp |
| 6,241,950 | B1 | | 6/2001 | Veelenturf et al. |
| 6,405,577 | B2 | * | 6/2002 | Hanashiro et al. ....... 73/23.31 |
| 6,592,254 | B2 | | 7/2003 | Gul |
| 6,941,193 | B2 | | 9/2005 | Frecksa et al. |
| 2002/0129668 | A1 | * | 9/2002 | Gamache et al. ....... 73/863.33 |
| 2004/0166679 | A1 | * | 8/2004 | Kishkovich et al. ....... 438/689 |

FOREIGN PATENT DOCUMENTS

WO  WO 02/063294  8/2002

OTHER PUBLICATIONS

U.S. Appl. No. 60/660,245, filed Mar. 10, 2006, Desrochers, Eric M.; Sharp Gordon.

* cited by examiner

*Primary Examiner*—Robert R Raevis
(74) *Attorney, Agent, or Firm*—Brian M. Dingman; Mirick O'Connell; DeMallie & Lougee (57) ABSTRACT

This invention details apparatus and methods for a unique integrated duct probe assembly system that enables multipoint sampling systems to cost effectively measure air parameters in partially confined locations such as ductwork, plenums, and air handlers with both remote and local sensors with a minimum of duct penetrations.

29 Claims, 9 Drawing Sheets

DUCT PROBE ASSEMBLY SYSTEM FOR MULTIPOINT AIR SAMPLING

CROSS REFERENCE TO RELATED APPLICATION

This application is a Divisional of co-pending application Ser. No. 11/312,164, entitled "Duct Probe Assembly System for Multipoint Air Sampling," filed Dec. 20, 2005, to Desrochers et al. and incorporated herein by reference, and for which priority is claimed under 35 U.S.C § 121.

FIELD OF THE INVENTION

The present invention relates generally to air sampling and, more particularly, to systems for measuring air characteristics with multipoint air sampling systems,

BACKGROUND OF THE INVENTION

As is known in the art, there are various applications where air is transported through a tube or pipe for sampling or measurement purposes. For example, an air quality or an environmental air parameter measurement system may have remotely located sensors instead of at the sensed environment. In addition, a sensor or a single set of multiple sensors may be used to sense a plurality of locations creating a measurement system known as a multi-location or a multipoint air sampling system. For one class of these systems, multiple tubes may be used to bring air samples from multiple locations to a centralized sensor(s). Centrally located air switches and/or solenoid valves may be used in this approach to sequentially switch the air from these locations through the different tubes to the sensor to measure the air from the multiple remote locations. These octopus-like systems sometimes known as star-configured or home run systems use considerable amounts of tubing. An example of such a star-configured system is described in U.S. Pat. No. 6,241,950, which is incorporated herein by reference. Other types of systems known to the art of air monitoring include those that are designed to monitor refrigerants and other toxic gases, which also are star-configured systems. Additionally, these types of star-configured systems have been used to monitor particulates in multiple areas such as clean room areas with a single particle counter. Generally, these types of systems, however, have historically not been applied to general air quality measurement applications, even though they could easily be adapted to do so.

Another multipoint sampling system known as a networked air sampling system uses a central 'backbone' tube with branches extending to various locations forming a bus-configured or tree like approach similar to the configuration of a data network. Air solenoids are typically remotely located proximate to the multiple sampling locations. Networked air sampling systems can also include remote and/or multiple-location air sampling through a tube or pipe for sampling locations in a building, outdoor air or ambient sampling, and sampling in smokestacks and exhaust air stacks. An exemplary networked air sampling system is described in U.S. Pat. No. 6,125,710, which is incorporated herein by reference.

The multipoint sampling systems which have been described may be applied to monitor a wide range of locations throughout a building, including any kinds of rooms, hallways, lobbies, interstitial spaces, penthouses, outdoor locations, and any number of locations within ductwork, plenums, and air handlers.

One characteristic of these multipoint sampling systems is that some parameters such as temperature in particular, but some other parameters as well such as ozone can not always be effectively measured from a remote location with a shared sensor. Furthermore, other parameters may be accurately measured at a remote location with a shared sensor but, for various reasons such as the need for more rapid sampling, may be preferred to be sensed locally at one or more of the sensed locations. In these situations, separate sensors and either distinct signal wires or a digital data communications network with cable, optical fiber or wireless links can be used to connect remote sensors such as temperature sensors to either the networked sampling system or possibly a building management system.

When these multipoint sampling systems are used to sample ductwork, plenums, air handlers or any other applications where flowing air in a partially contained area such as a duct or pipe is to be sampled and measured with a remote sensor, a tube or hollow duct probe must be inserted into the duct or partially contained space to withdraw a sample. Additionally however, a separate temperature or other parameter sensing probe or probes are needed to make whatever local sensor measurements are desired from these ducts or partially enclosed areas. The use of multiple separate probes for both sensing and drawing air samples leads to extra costs as well as more duct penetrations that unfavorably increase the installation expense of the multipoint sampling system.

As such this invention provides solutions to enable multipoint air monitoring systems to cost effectively and reliably monitor air parameters both locally and remotely within many of the partially confined locations within a building, and is especially suitable but not limited to applications involving monitoring air parameters within ductwork, plenums, and air handlers.

SUMMARY OF THE INVENTION

It is therefore a primary object of this invention to provide an integrated duct probe assembly system that enables multipoint sampling systems to measure air parameters in partially confined locations such as ductwork, plenums, and air handlers.

It is a further object of this invention to provide a duct probe assembly that enables cost effective measurement of air parameters in partially confined locations with both remote and local sensors with a minimum number of duct penetrations.

This invention details apparatus and methods for a unique integrated duct probe assembly system that enables multipoint sampling systems to cost effectively measure air parameters in partially confined locations such as ductwork, plenums, and air handlers with both remote and local sensors with a minimum of duct penetrations.

One preferred embodiment of the invention comprises an air parameter sensor, such as a solid duct temperature probe known as a thermowell, that is generally constructed with a hollow internal space or sampling tube that serves as a means to draw a sample from the flowing air stream or air space being sampled by a multipoint sampling system. Additional embodiments of this invention incorporate one or more sensors within the probe assembly for detecting air parameters other than temperature. These one or more alternate sensors may either be incorporated with the probe assembly in addition to a temperature sensor, or the probe assembly may include one or more alternate sensors and not include a temperature sensor. The air parameter sensors and optional electronics incorporated with the duct probe assembly may either be attached to the portion of the duct probe's air sampling tube that is inserted into the duct, or one or more air parameter sensors may be housed in an enclosure outside the duct or plenum. Both the sampling tube and the air parameter sensor may be connected to the multipoint sampling system or the sampling tube may be connected to the sampling system while one or more of the one or more air parameter sensor(s) (optionally including temperature) are connected to either the multipoint sampling system or a building management system (or equivalently some other data monitoring or control system) or both.

More specifically, the preferred embodiment of the probe assembly system of the invention, for extracting an air sample from a flowing air stream, comprises: a first tube which is at least partially immersed in the flowing air stream and is adapted to enable the air sample to pass through the first tube to a second tube that is in communication with a multipoint sampling system; and at least one sensor assembly that is adapted to sense characteristics of the air sample and is attached to the first tube to sense at least one characteristic of the flowing air stream, wherein the first tube may extract the air sample isokinetically, and wherein the first tube may be adapted to extract the air sample to compensate for any effects of an anisokinetic sampling of the flowing air steam.

The sensor preferably comprises a temperature sensor, wherein the temperature sensor is housed within a thermowell that is fixed to the first tube, wherein the thermowell surrounds at least a portion of the first tube. The temperature sensor may comprise a sensing element that extends along at least half of the portion of the length of the first tube that is immersed in the flowing air stream.

One or more of the sensors may also comprise a variety of sensors including, but not limited to an ozone sensor and/or a humidity sensor.

The probe assembly of the invention is adapted to sense a flowing air stream that is located inside of a building's air handling unit, wherein the flowing air stream may be located inside a mixed air plenum of the building's air handling unit such as inside a portion of a duct system of a building's HVAC system. The first tube preferably samples the flowing air stream from a plurality of sampling holes, wherein the sampling holes in the first tube are preferably located at positions along at least a portion of a length of the first tube, and wherein each air sample drawn from a given sampling hole has a volume that is approximately equal to the volume of a cross section of a predefined space though which the flowing air stream is moving. At least one of the sensors may comprise sensor elements that are located in close proximity to at least two of the sampling holes. The probe assembly may comprise a plurality of the first tubes that each comprise at least one sampling hole that samples the flowing air stream, wherein the sampling holes in the plurality of first tubes are located at positions within the flowing air stream so that each air sample drawn from a given sampling hole has a volume that is approximately equal to the volume of a cross section of a predefined space though which the flowing air stream is moving.

At least one of the sensors of the probe assembly of the invention preferably generates a signal that is in direct communication with the multipoint sampling system, wherein at least one of the sensors generates a signal that is in direct communication with a building management system.

The probe assembly system of the invention may further comprise a probe housing, wherein at least one of the sensors is in direct communication with a signal conditioning circuit that is located within the probe housing, and the signal conditioning circuit is in direct communication with the multipoint sampling system and/or a building management system.

As noted, the sampling tube may have multiple sampling holes to obtain a better average of the duct conditions in multiple locations. Similarly the invention may also include sampling probes with multiple sensors at different locations on the duct probe to get a better average sensor measurement. Alternatively, an averaging measurement device such as a temperature sensing element consisting of a long sensing element wire can be wrapped around or run along at least a part of the length of the sampling tube to obtain a better average measurement of the airflow throughout the duct.

Another preferred embodiment of the invention, adapted for larger sized areas or ducts that need to be measured, comprises multiple duct probes that are utilized to obtain a two dimensional measurement of the duct or sensed area versus a measurement in only one dimension.

For those duct probes with multiple sampling holes and or multiple probes, the location of the sampling holes is beneficially located to produce sampling of roughly equal areas of the duct or cross section of the area being sensed.

The preferred method of the invention for using a probe assembly for extracting an air sample from a flowing air stream, generally comprises the steps of: providing a probe assembly comprising, a first tube which is at least partially immersed in the flowing air stream through which the air sample passes and is transferred to a second tube that is in communication with a multipoint sampling system; and at least one sensor assembly that is attached to the first tube and that is adapted to sense at least one characteristic of the flowing air stream; and sensing at least one characteristic of the flowing air stream, wherein the first tube may extract the air sample isokinetically and to at least partially compensate for any effects of an anisokinetic sampling of the flowing air steam.

At least one of the sensors preferably comprises a temperature sensor wherein the temperature sensor is contained within a thermowell that is attached to the first tube, wherein the thermowell surrounds the first tube, and/or wherein the temperature sensor has a sensing element that extends along at least half of the portion of the length of the first tube that is immersed in the flowing air stream. The flowing air stream may be located inside of a building's air handling unit such as a mixed air plenum of the building's air handling unit and/or inside a portion of a duct system of a building's HVAC system.

The first tube used in the method preferably samples the flowing air stream from a plurality of sampling holes, wherein the sampling holes in the first tube are located at positions along at least a portion of the first tube within the flowing air stream so that each air sample drawn from a given sampling hole has a volume that is approximately equal to the volume of a cross section of a predefined space through which the flowing air stream is moving. The probe assembly may further comprise a plurality of first tubes wherein each of the first tubes comprises at least one sampling hole that is adapted to sample the flowing air stream, wherein at least one of the sensors comprises sensor elements that are located in close proximity to at least two of the sampling holes. The sampling holes of the first tubes may be located at positions along at least a portion of the first tube within the flowing air stream so that each air sample drawn from a given sampling hole has a volume that is approximately equal to the volume of a cross section of a predefined space though which the flowing air stream is moving.

At least one of the sensors preferably generates a signal that is in direct communication with a building management system. Still further, at least one of the sensors is preferably in direct communication with a signal conditioning circuit that is housed within the probe assembly, and wherein the signal conditioning circuit is in direct communication with a building management system.

As noted, the temperature sensor may be contained within a thermowell that is attached to the first tube, wherein the thermowell surrounds the first tube and wherein the temperature sensor may have a sensing element that extends along at least half of the portion of the length of the first tube that is immersed in the flowing air stream.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS AND METHODS

The invention features a multipoint air sampling system. A preferred embodiment of the system features a probe assembly 400, which is generally shown and referred to in FIG. 4. The multipoint air sampling system of the invention preferably combines hollow tube 401 and sensor element 402 into one common probe assembly 400. Probe assembly 400, while adapted for the multipoint air sampling system of the invention, may also be advantageously used in more conventional air sampling systems as well.

Figure 1:
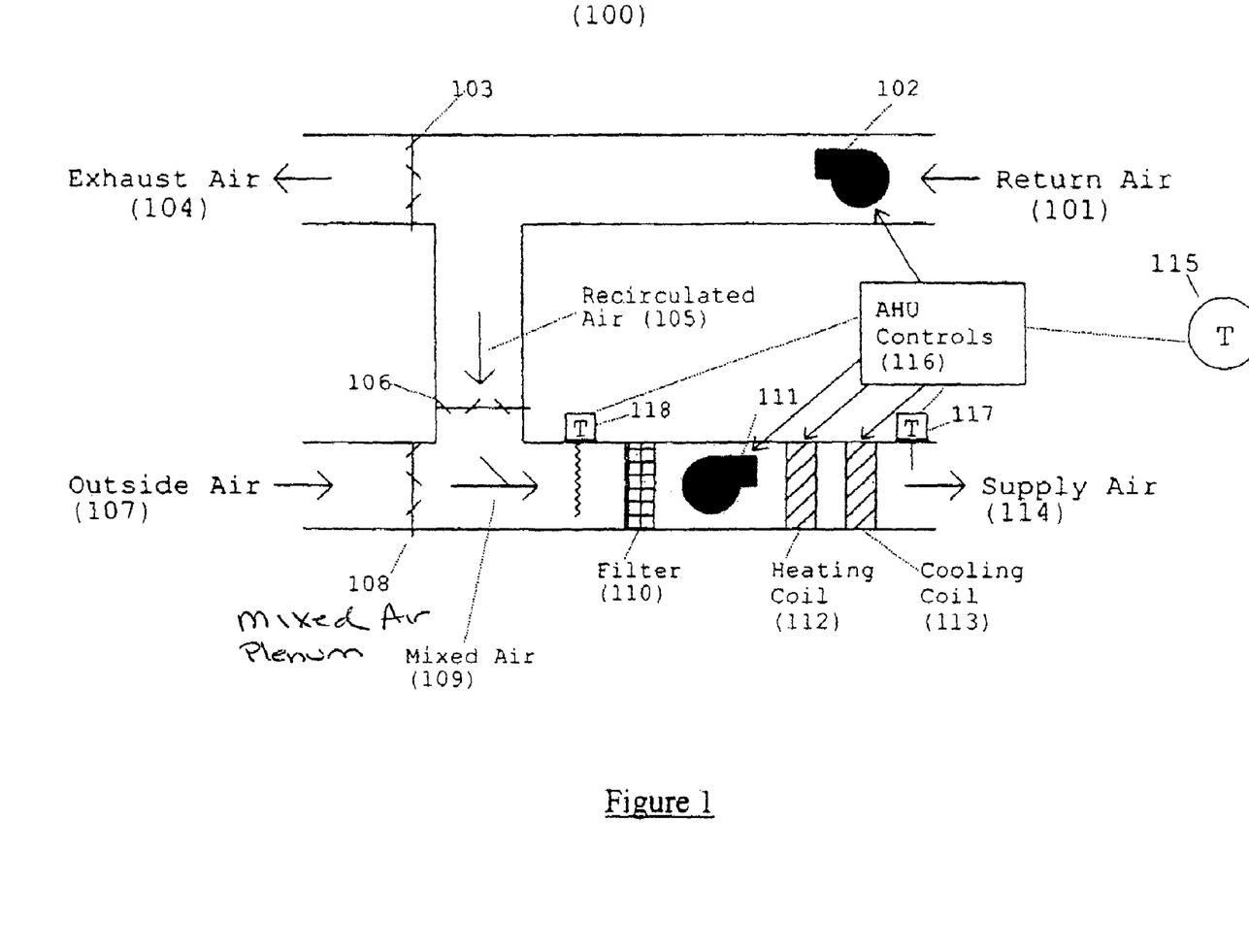
FIG. 1 is a schematic diagram of a typical air handling unit and its associated heating, cooling and controls components indicating potential locations for air sampling probes.

A typical ventilation system for a building involves one or more air handling units and associated fan systems which, together, perform many critical HVAC functions including: maintaining building pressurization, providing sufficient amounts of fresh air to occupants, controlling moisture levels within the building, controlling airborne dust or particulate levels, and the control of building air temperature. FIG. 1 depicts the classic "H" style fan system topology. Such systems supply conditioned supply air 114 to spaces or rooms that form a zone within the building. In a given building there may be one or multiple zones, and in some cases a single system such as 100 can be applied to multiple zones. In other cases systems such as 100 can be dedicated to a single zone and therefore it is not uncommon to have a multiplicity of systems such as 100 within a building having multiple zones. In most cases the supply air 114 (also referred to as discharge air) is ducted to multiple locations within a building and if all of these locations are to be treated as a common zone it is typical to have all of the air conditioning performed by system 100. In such cases, it is common to locate a single thermostat or sensing element (115) at a location within the zone, which in turn is wired to an electronic air handler unit (AHU) controller 116 that provides the control functions to system 100. With the single zone system described, the temperature of supply air 114 is controlled by AHU controller 116 which appropriately controls the AHU to heat or cool the air using heating coil 112 and cooling coil 113 so that supply air 114 is at the correct temperature to maintain the desired temperature within the space in which thermostat 115 is located. In many instances, all of the control functions that perform this temperature control operation are located within AHU controller 116, and sensing element 115 is simply a temperature sensor. In other instances, sensing element 115 is a complete thermostat that provides both temperature set point functions and control functions.

In instances where system 100 serves multiple zones, supply air 114 is typically preconditioned to a predetermined temperature of 55 degrees Fahrenheit. A reheat coil is applied within the distribution ductwork for each zone in which a dedicated thermostat or controller is placed to separately maintain zone temperatures. In such an arrangement, duct temperature probe 117 is used to monitor the supply air 114 temperature so that AHU controller 116 can maintain the temperature to 55 degrees Fahrenheit or any other suitable set point by regulating heating coil 112 and cooling coil 113.

HVAC systems typically utilize duct probe sensors having a thermal well construction, in which the sensor is sealed or embedded within a thermally conductive tube (that is typically metal) and in practice is immersed in the airflow stream. The thermally conductive tube tends to have an averaging affect on the temperature sensed by the embedded sensor, which is commonly an electrically resistive sensor, such as a thermistor or a resistance temperature detector (RTD).

Although the typical design of a thermowell-style duct air temperature sensor provides a level of averaging to the temperature measurement, a common problem with such measurements is that air temperatures can vary significantly across a cross section of ductwork. This is usually not a big problem with supply air 114, which is usually uniform, but it can be a problem with mixed air 109. Mixed air 109 in mixed air plenum 108 is the result of the outside air (107) and recirculated air 105 flow streams converging, and it is often the case that these flow streams are at two very different temperatures. For example, recirculated air 105 is a portion of the return air 101 that is removed from a zone or zones that could be at 68 degrees Fahrenheit and, on a winter day this air 105 could be mixed with outside air 107 that is at a temperature of 40 degrees Fahrenheit. The actual resultant mixed air average temperature is dependant on the volume flow rate of the outside air 107 relative to the amount of recirculated air.

The air temperature, in such instances, will vary greatly over the cross section of the ductwork located immediately upstream from filter 110 due to incomplete mixing.

It is often desirable to measure mixed air temperature for a variety of reasons including economizer control function and airflow measurement functions. In addition, there are many other applications involving temperature measurement in which duct temperature varies along the duct cross section. To accomplish this, duct averaging temperature sensor 118 is used. Generally, a duct averaging temperature sensor is composed of an element, like a platinum wire, or a number of elements that are made to span the cross section of the duct from which a measurement is to be made. Some examples of these types of sensors are described in U.S. Pat. Nos. 6,592,254 and 4,547,079.

In addition to normal room monitoring applications, the multipoint air sampling system of this invention may be used to monitor locations in systems such as 100, or in general, any system involving air flow delivery including any type of air handling system topology known to those skilled in the art. Some of these additional air handling topologies include but are not limited to: any type of single pass 100% outside air system, dual duct systems, dedicated outside air systems, fan coil systems, and virtually any system involving air delivery. These applications include air flow delivery to any kind of environment including but not limited to: locations throughout office or commercial buildings, labs, bio-chemistry facilities, hospital environments, operating rooms, patient rooms, pharmaceutical environments, aseptic processing areas, industrial environments, bio-safety facilities, vivariums, clean rooms, and even residential environments. The application of a multipoint air sampling system enables sensing capabilities for a wide variety of parameters limited only by the type of shared sensors that can be used, which can be valuable for purposes of a variety of control strategies, air quality monitoring, or system performance monitoring purposes. For example, some of these sensing capabilities include but are not limited to sensing for $CO_2$, CO, NOx, VOC's, particulate matter (such as PM2.5, PM10, and even microfine particles), moisture (dew point temperature), $NH_3$, mold spores, chemical or biological terrorist threat materials, radon gas, and even differential pressure. However, despite the capabilities that the shared sensors in a multipoint air sampling system can provide, there are some parameters, such as temperature, and highly reactive gases such as ozone, which may not transport well, based on the transport media and therefore, may not be practical to sense with a remote sensor. Nevertheless, there are many cases where it will be advantageous for a multipoint air sampling system to incorporate these parameters along with the data it generates from its shared sensor(s), particularly in cases where a third parameter is based on a calculation involving a first hard to transport parameter, such as temperature, and a second parameter measured by a shared sensor, such as dew point temperature. For example, if a multipoint air sampling system incorporates a hygrometer (measuring dew point temperature) as a shared sensor along with a temperature sensor at the sampling point, a combined measurement of enthalpy, RH, or other psychometric properties can be computed.

Figure 2:
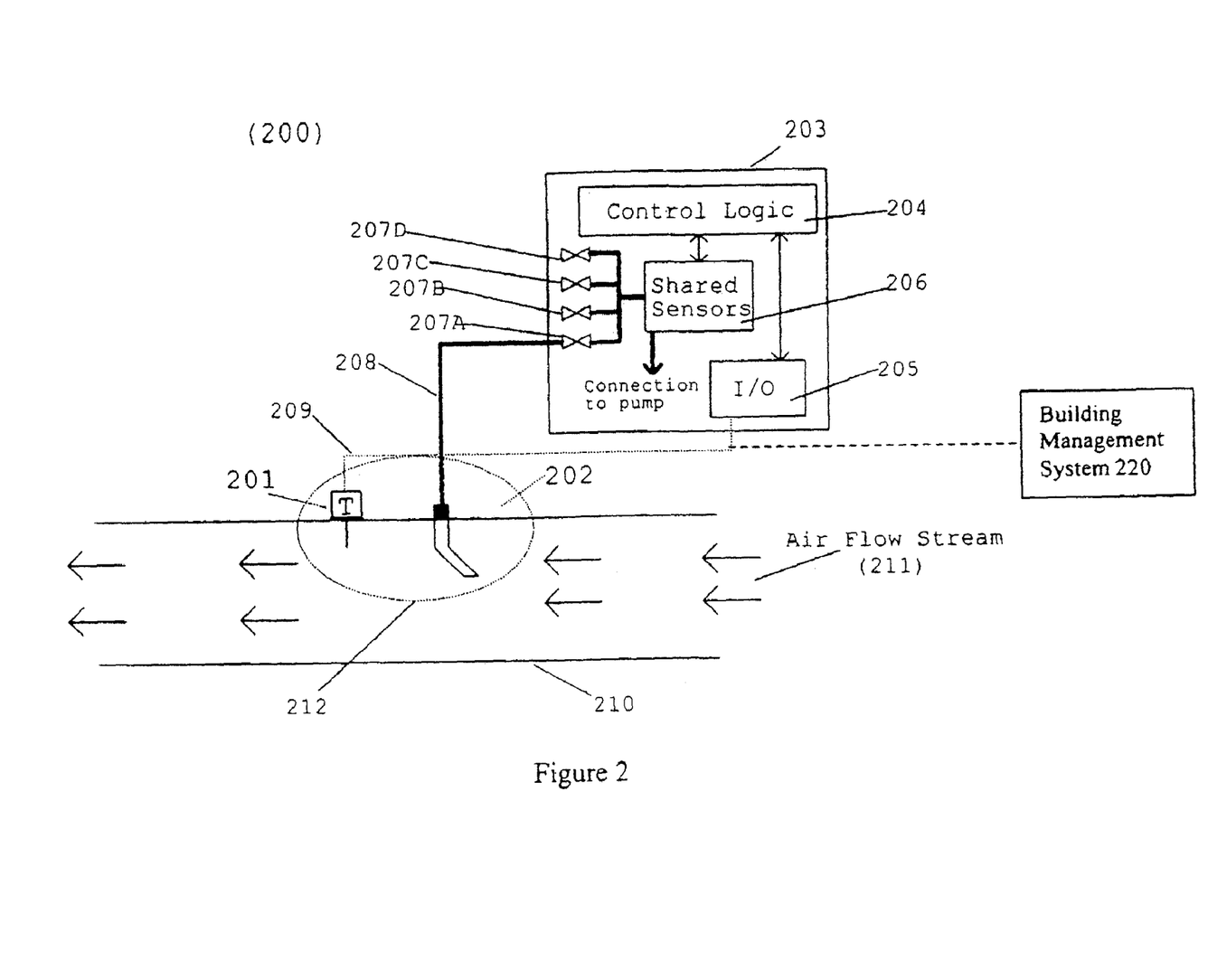
FIG. 2 is a schematic diagram of a prior art technique for obtaining an air sample and a temperature measurement from a duct sampling location.

FIG. 2 is an illustration of a prior art technique for obtaining an air sample and a temperature measurement from a duct sampling location. This could be a duct location anywhere within a system such as 100, or it could be any duct location pertaining to any other type of ventilation system configuration.

As shown in 200, two physically separate probes, a sensor probe 201 and an air sampling probe 202, are attached to the duct 210 in order to obtain the combined measurement of temperature as well as other parameter(s) from the airflow stream 211. The other parameters are based upon the types of shared sensors 206 used within multipoint sampler 203. For example, the shared sensors could include $CO_2$, CO, a hygrometer, and other sensors. Multipoint air sampler 203 could be a star-configured multipoint air sampling system like that described in U.S. Pat. No. 6,241,950, it could be a multipoint air sampling like that described in U.S. Pat. No. 5,292,280, it could be a refrigerant and toxic gas monitor adapted for this purpose such as the Vulcain Inc. multipoint sample draw gas monitor model number VASQN8X, it could be a multiplexed particle counter such as the Universal Manifold System and Controller as made by Lighthouse Worldwide Solutions, Inc. coupled with one of their particle counters such as their model number Solair 3100 portable laser based particle counter or an obscuration based particle sensor, or it could be a networked air sampling system such as that described in U.S. Pat. No. 6,125,710.

As shown in FIG. 2, duct probe 202, which is a hollow first tube that penetrates the duct 210, is immersed in airflow stream 211. The air sample is extracted from air flow stream 211 through first tube 202 and is transferred to a second tube 208 through which it is transported to sampling valve 207A, which valve may or may not be contained within 203, depending on the type of multipoint air sampling system used. Also, depending on the type and size of the multipoint air sampling system, 203 may utilize more or less valves than 207A, 207B, 207C, and 207D. Regardless of the type of system 203, valves 207 will usually be sequenced so that shared sensors 206 will be exposed to one air sample at a time. In turn the system 203 may be connected to a Building Automation or Building Management System to communicate the sampled data associated with each sampled location 212 for both monitoring and or building control purposes.

The sensor probe 201 in FIG. 2 can be a thermowell style sensor assembly or any number of other types of commercially available temperature sensor probes for ducts. Generally, this probe will be similar to that which is suitable for use as probe 117. A thermowell approach is usually used for higher-end applications where it is undesirable to remove the portion of the probe that penetrates the duct. Thermowells house the sensor element, such as an RTD used for the temperature measurement, and allow the sensor to be removed if for example it fails and needs to be replaced, without having to remove the outer housing from the duct on which it is mounted. This is important for some applications, where the air stream being monitored is contaminated in some way. For example, such an air stream could be the exhaust air flow from a fume hood in a laboratory, or it could be connected to the exhaust air duct from an explosion proof room.

In more typical applications the temperature-sensing element (such as an RTD or thermistor, for example) is permanently affixed within a probe housing which is usually a metal tube that is open on one end and closed at the other. There are many manufacturers of such probes, such as Dwyer Instruments, Precon Inc., Kele Inc., Tempco Controls, Honeywell International, and Pyromation Inc., to name a few. For example, sensor probe 201 could be an assembly like the HD30K, by Kele, Inc., which has options for both a temperature sensor and an RH sensor. The signal outputs of Sensor probe 201 with its one or more environmental sensors are connected to the multipoint sampling system 203 through electrical cable 209. This connection can be either an analog signal connection, or may be a digital signal on dedicated wires or addressed digital data information transferred on a networked or dedicated data communications cable. In some cases the cable 209 may go directly to a building management system 220, which typically provide some form of at least monitoring and or control of at least some portion of the building's heating, ventilating and air conditioning (HVAC) systems, or equivalently to another building data monitoring or control system, either instead of to the multipoint sampling system or in addition to the multipoint sampling system.

Figure 3:
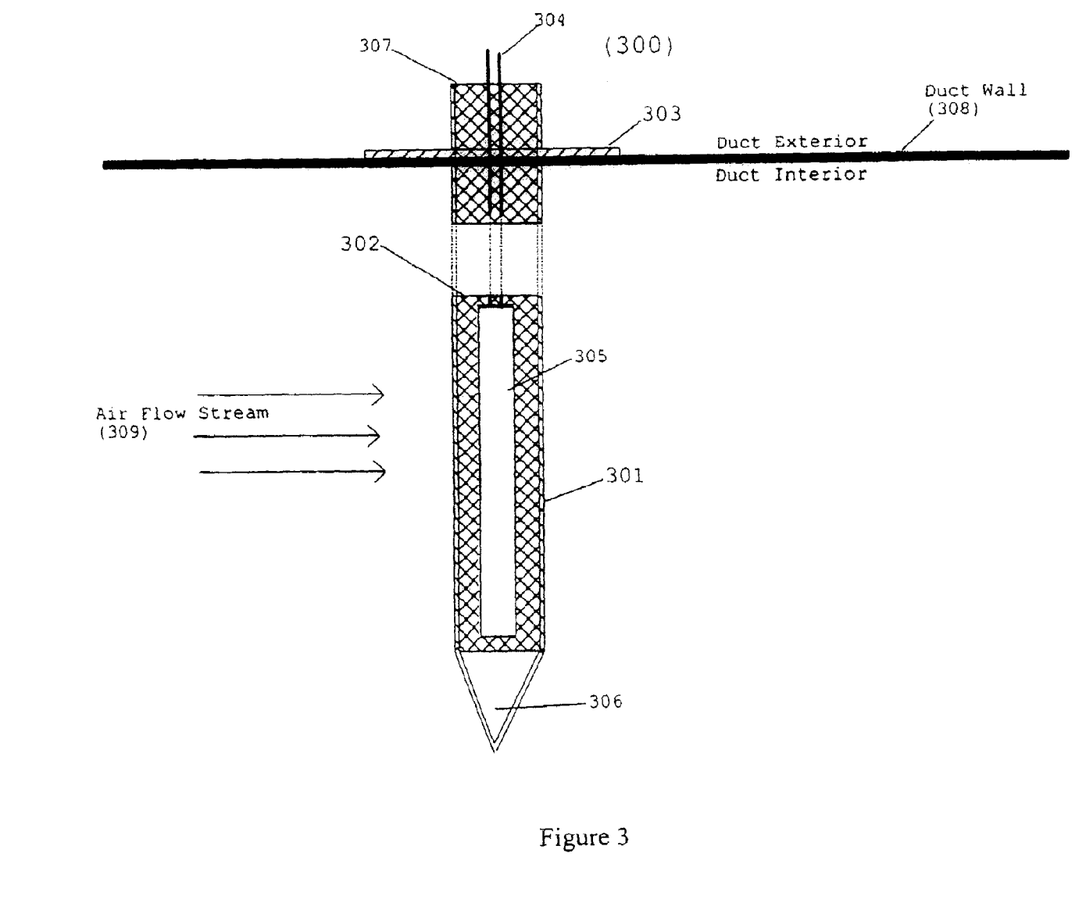
FIG. 3 is a cross-sectional view of a typical prior art probe used for temperature measurement of an airflow stream.

FIG. 3 depicts a generalized view of a typical prior art probe used for temperature measurement of an air-flow stream such as 211. The assembly 300 is a simple arrangement which includes tubing section 301 that is usually metal. The tubing 301 is closed at one end 306 and open at the other 307. Typically, a hole is drilled into the duct wall 308 onto which the probe is mounted, with the closed end 306 inserted into the flow stream. Flange 303 is an example of one of many types of possible mounting mechanisms. In this case, for example, one or several sheet metal screws could be driven through flange 303 into duct wall 308 in order to secure the duct probe 300 in place on the duct. Such an assembly 300 can support any variety of sensor elements that can for example be any type of temperature sensing element such as a platinum or nickel RTD (in wire or other form), a thermistor, or a solid state sensor. Also, element 305 can be a discrete sensor element using only a small portion of the overall length of tube 301, or it can span a large fraction of the entire length of 301, but typically does not exceed the length of 301. In order to assure that the temperature that is measured by element 305 is substantially the same as that of the airflow stream 309 it is important to provide a highly thermally conductive path between element 305 and the surface of 301, which is in fluid communication with 309. To accomplish this, a thermally conductive filler 302 is included with assembly 300. For this purpose thermally conductive filler 302 is usually, a two-part epoxy. This filler 302 also maximizes sensor response time and protects the sensor element from moisture. Additionally, it should be clear to those skilled with air distribution systems that assembly 300 can be applied to ducts of any shape and sizes, the most common shapes being round, rectangular, oval, and square.

The temperature probe assembly 300 provides a signal output from sensor element 305 via conductors 304, which may be connected locally to a signal conditioning circuit or 304 may be routed to a remote monitoring and signal-conditioning device. For example conductors 304 could be routed to a unitary controller that is monitoring and possibly controlling the supply air 114 within a system 100.

Using the two probes 201 and 202 as shown in 200 poses several problems from an installation standpoint because two penetrations of duct 210 are required to support 201 and 202, and the time and cost of the labor associated with both making the penetrations (drilling holes) and mounting the two probes 201 and 202 is undesirable. Similar to this, the cost of having two probe assemblies 201 and 202 is undesirable.

In addition, accuracy issues can result when measuring a parameter that requires both a measured value from sensor probe 201 and a sensed parameter from a shared sensor 206 from an air sample taken through probe 202, if the sensed parameter from 201 is not the same at the probe location 202 as it is at the location of 201. For example, as described in U.S. Provisional Patent Application No. 60/660,245, if a shared sensor 206 is a hygrometer measuring dew point temperature from an air sample taken through 202, specific psychrometric properties of the air flow stream 211 can be determined such as enthalpy, relative humidity, and humidity ratio. The problem with doing this using a probe 202 and a separate probe 201 for temperature measurement is that air temperature can easily vary by a few degrees along short distances along either the length or the cross section of an airflow stream 211, and a few degrees of error in a temperature measurement when making psychrometric calculations can significantly affect the accuracy of the calculation, depending on the moisture content of the air sample.

Also, in practice it can be very difficult to physically locate two probes 201 and 202 at the same location on a duct 210 as building construction and equipment layout often compete with the space required for running ductwork. What is needed is a more compact alternative to the space required for mounting and making connections to probes 201 and 202.

Figure 4:
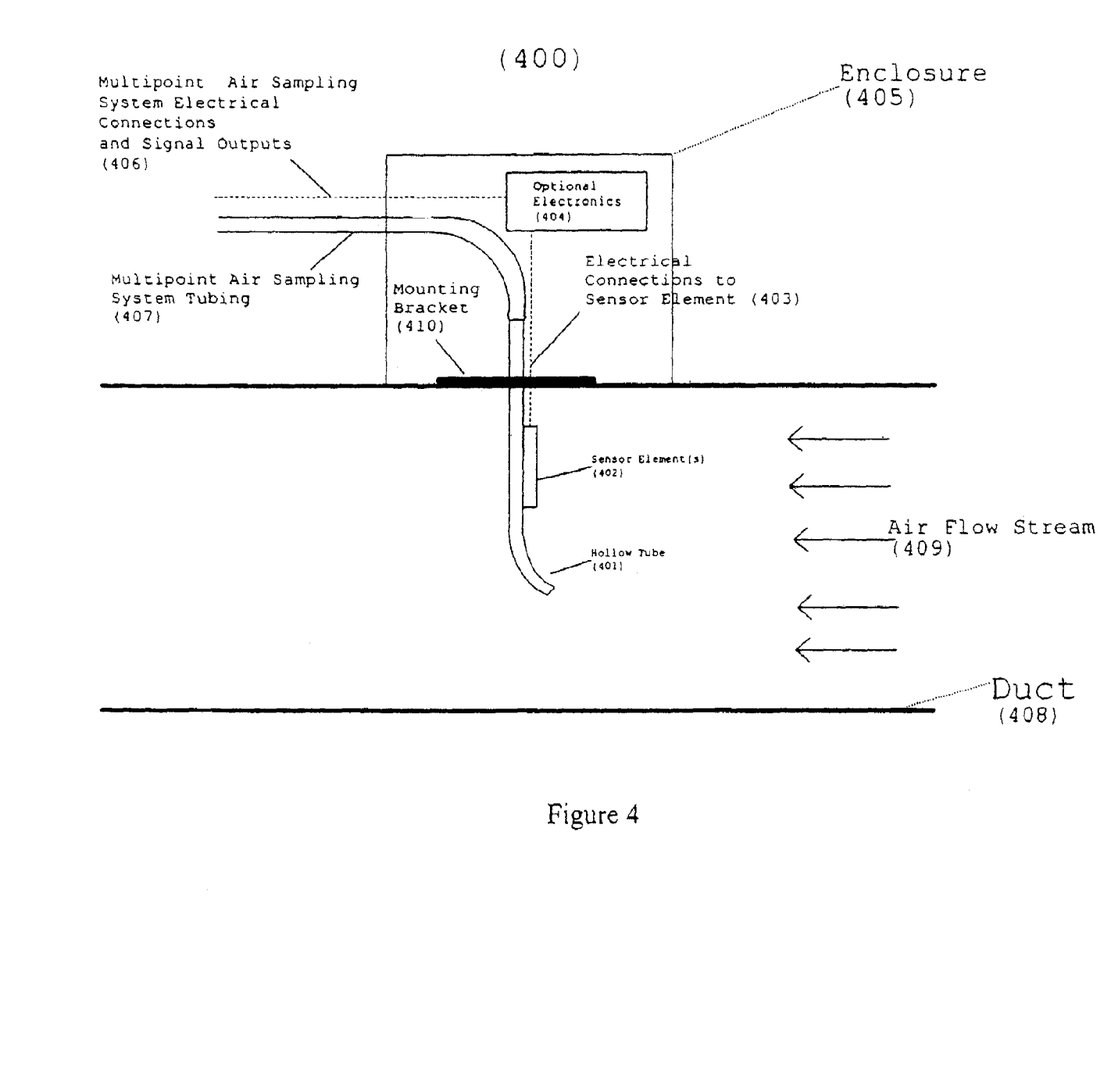
FIG. 4 is a schematic diagram of a preferred embodiment of the multipoint air sampling system of the invention which combines a sensor probe and an air sampling probe into one common probe assembly.

FIG. 4 depicts several aspects of the current invention which combines sensor probe 201 and probe 202 into one common probe assembly 400. As shown in FIG. 4, the assembly comprises: a first hollow tube 401 which is at least partially immersed in air flow stream 409 through which tube 401, air samples of air flow stream 409 can be taken; sensor element(s) 402, which can be an assembly of one or a plurality of sensors that are either directly or indirectly mounted to first tube 401; optional electronics 404 which may provide signal conditioning to sensor element(s) 402 as well as power, signaling, and/or communication functions back to an air sampling system 450 or alternatively to, or in addition to building management system 460 or another air parameter monitoring or control system; optional enclosure 405; and a connection to a second tube 407 which is used to transfer air samples from first tube 401 back to a multipoint air sampling system 450. This multipoint sampling system 450 could be a star-configured multipoint air sampling system like that described in U.S. Pat. No. 6,241,950, it could be a multipoint air sampling system like that described in U.S. Pat. No. 5,292,280, it could be a refrigerant and toxic gas monitor adapted for this purpose such as the Vulcain Inc. multipoint sample draw gas monitor model number VASQN8X, it could be a multiplexed particle counter such as the Universal Manifold System and Controller as made by Lighthouse Worldwide Solutions coupled with one of their particle counters such as their model number Solair 3100 portable laser based particle counter or an obscuration based particle sensor, or it could be a networked air sampling system such as that described in U.S. Pat. No. 6,125,710.

Hollow tube 401 can be of any practical diameter and length depending on the physical limitation of the duct 408 onto which it is mounted. The cross section of the tube 401 can be round, square, or any shape, however, it is generally easiest to provide a round penetration (hole) in the duct 408 to receive tube 401, so it is beneficial that 401 be round, thus simplifying installation and making it easier to seal the tube 401 to a duct 408.

In practice, it is also advantageous to minimize the outer diameter of hollow tube 401 to a practical diameter which will require a small mounting hole in relation to the diameter of the duct 408 on which 400 is to mount.

The sensor element(s) 402 may be connected directly to the multipoint sampling system 450 through line 406 which is a cable containing electrical connections and the sensor's analog, digital, or addressed network communications data. Alternatively, the sensor elements may be connected to optional signal processing electronics 404 through cable 403. The optional electronics 404, which may provide signal conditioning and other interface functions to sensor element(s) 402, are then connected to the sampling system 450 through cable 406. Alternatively the cable 406 may connect the sensor element(s) 402 or optional electronics 404 to a building management system or any environmental data monitoring or control system 460 either instead of the multipoint sampling system 450 or in addition to 450.

Although it is generally advantageous to provide electrical connections 406 to convey information from sensor element 402 to multipoint sampling system 450, in one embodiment, connection 406 is a wireless connection. This is useful, for example, in applications where it is necessary to locate 401/402 in an intrinsically safe environment, or in other applications where it is undesirable (whether it be because of safety, logistics, or cost reasons) to connect wires between the duct probe assembly and multipoint sampling system 450 and/or building management system 600. This may be carried out by embedding a wireless transmitter in sensor element 402 or, preferably, within optional electronics 404. This transmitter could be part of a wireless network that multipoint sampling system 450 and/or building management system 460 are also connected to, or this could be a point-to-point wireless connection.

Additionally even though the pictorial of hollow tube 401 in FIG. 4 shows a bend in the end of this tube as it sits in the air flow stream 409, the embodiments of this invention are not limited to this, as the tube 401 may be straight or articulated in any direction within the air flow stream 409. Generally however an exemplary embodiment would have the tube 401 bent at a right angle directly facing the direction of the airflow stream 409 or may be placed at a slight angle to the oncoming flow 409 as shown in FIG. 4 to correct for potential flow velocity mismatches of the flowing air stream vs. the velocity of the sampling air stream through the hollow tube 401. One of the factors influencing the choice of the position of the hollow tube 401 relative to the air flow stream 409 relates to the issue of isokinetic sampling. To get a true sampling of the concentration of particles, particularly larger particles greater than, for example, 5 microns, it is best to use isokinetic sampling. In this type of sampling, the sampling duct probe, or in our case the hollow tube 401, is directed into the flowing air stream 409 and the velocity of the air flowing through the tube 401 is matched to the velocity of the air flow 409 using one of several techniques well known to those skilled in the art of isokinetic sampling.

If instead, the air velocity through the hollow tube 401 is fixed or unrelated to the velocity of the flowing air stream 409, then the effects of this type of anisokinetic sampling can generate a higher or possibly lower representation of the concentration of the larger sized particles in the air flow stream 409. As a result a preferred embodiment has the hollow tube 401 bent into the direction of the airflow stream 401 at a 30 to 45 degree angle to partially compensate for the effects of anisokinetic sampling when the airflow 409 velocity is higher than the sample flow velocity through the hollow tube 401. Alternatively, the least impact of anisokinetic sampling is seen for higher or lower airflow 409 velocities when the hollow tube is pointed directly into the air flow stream 409. Finally, if it is desired to reduce or filter out larger particles such as dust, the hollow tube 401 may be placed at right angles to the airflow stream 409 to enhance the effects of anisokinetic sampling or even to point the hollow probe opening 180 degrees away from the airflow stream 409 altogether.

Figure 5:
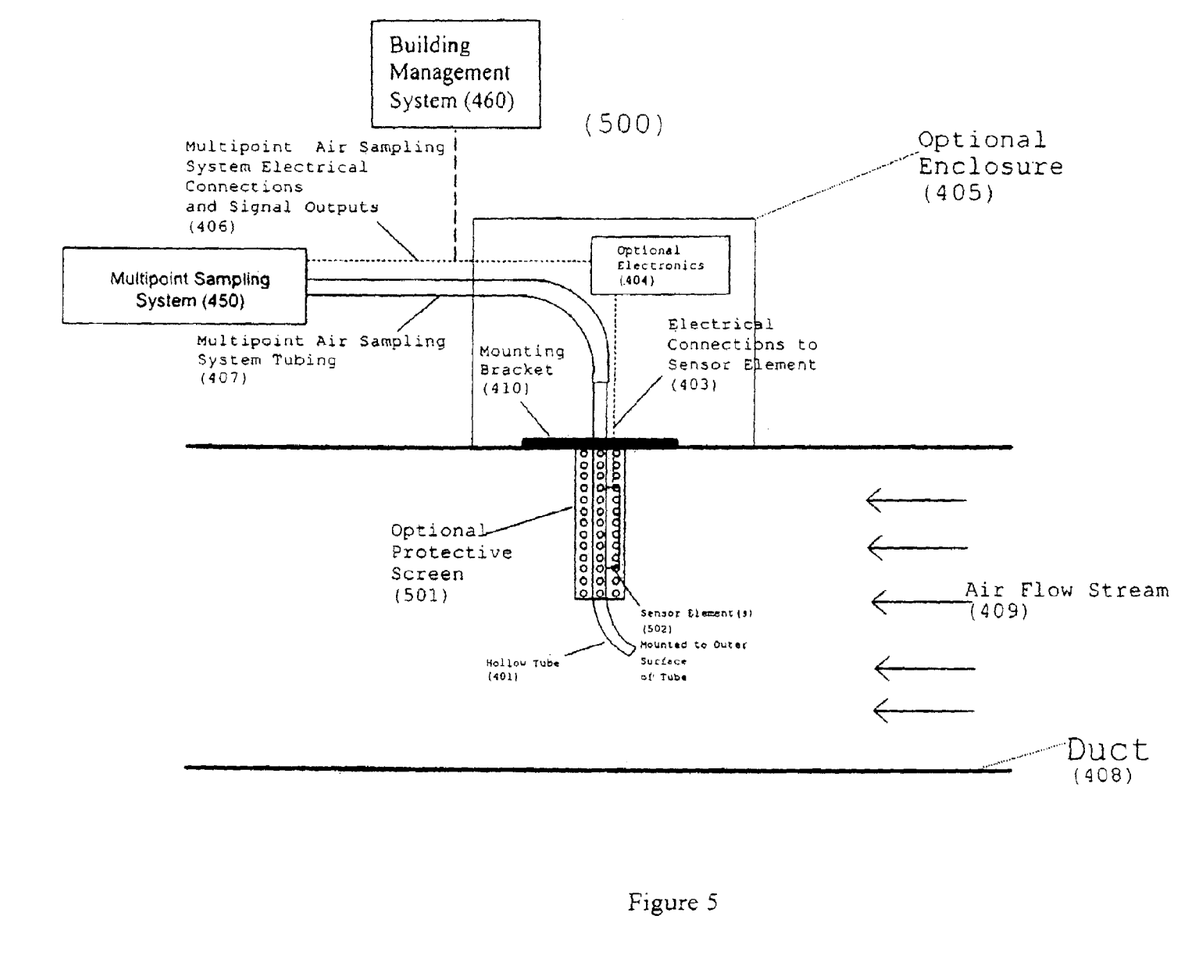
FIG. 5 is a schematic diagram of a preferred embodiment of the invention that combines a sensor probe and an air-sampling probe into one common probe assembly with an optional protective screen.

The sensor element 402 may be a combination of one or more sensors that are either directly or indirectly mounted to tube 401. For example, sensor(s) 402 could include but is not limited to one or more of an ozone sensor, temperature sensor, or relative humidity (RH) sensor mounted on the outer surface of the hollow tube 401, and thus directly exposed to the air flow stream as shown in FIG. 5 as sensor element(s) 502. In addition, one or a combination of these sensors can be either directly mounted to or connected by wires to a circuit board used to provide signal conditioning to one or more of these sensors, and such a circuit board could be mounted directly to hollow tube 401, either disposed within the air flow stream 409, with or without optional protective screen 501 covering it, or such a circuit board could be disposed within hollow tube 401, or such a circuit board could be placed on the outside of duct 408 as shown in FIGS. 4 and 5 as part of optional electronics 404. In addition, there can be any number of circuit boards used for conditioning the signals from the various sensors 402, so that some or each of the individual sensors comprising 402 can have dedicated signal conditioning circuitry on circuit boards dedicated to each sensor. In addition, any of the various circuit boards that are mounted within the duct 408 on hollow tube 401, or any of the various circuit boards that are disposed within hollow tube 401 may communicate wirelessly to optional electronics 404.

As shown in FIG. 5, if one or more elements 502, are mounted on the outer surface of hollow tube 401, an optional protective screen 501 may be provided. Here, optional protective screen 501 may be a perforated hollow cylinder that is rigid enough to protect sensitive sensor elements. Optional screen 501 may be made out of any material, but will preferably be made of metal, such as anodized aluminum or another suitable metal or coated metal. Metal is preferred (due to its thermal conductivity) when sensor element(s) 502 is required to make thermal measurements such as RH and temperature measurements. In addition, when sensing for volatile organic compounds (VOC's) in the air sample drawn through first tube 401 and presented to the multipoint air sampling system 450 through tube 407, it is important that the optional protective screen, sensor elements 502, and hollow tube 401 are made of materials that will not absorb or outgas VOC's.

If a temperature sensor is to be employed as part or all of sensor element 402 or sensor element 502 it may consist of any type of temperature sensing element such as platinum or nickel RTD (in wire or other form), a thermistor, a thermocouple, or a solid state sensor. A preferred embodiment would employ a temperature sensing wire element that could be wrapped in a spiral fashion around the hollow tube 401 over a selected portion of, or over most of the length of the hollow tube 401 to get a good average temperature measurement in the duct. If the hollow tube is flexible or bendable it is advantageous for the sensing element 402 or 502 to bend to accommodate the movement of the hollow tube 401.

Figure 6:
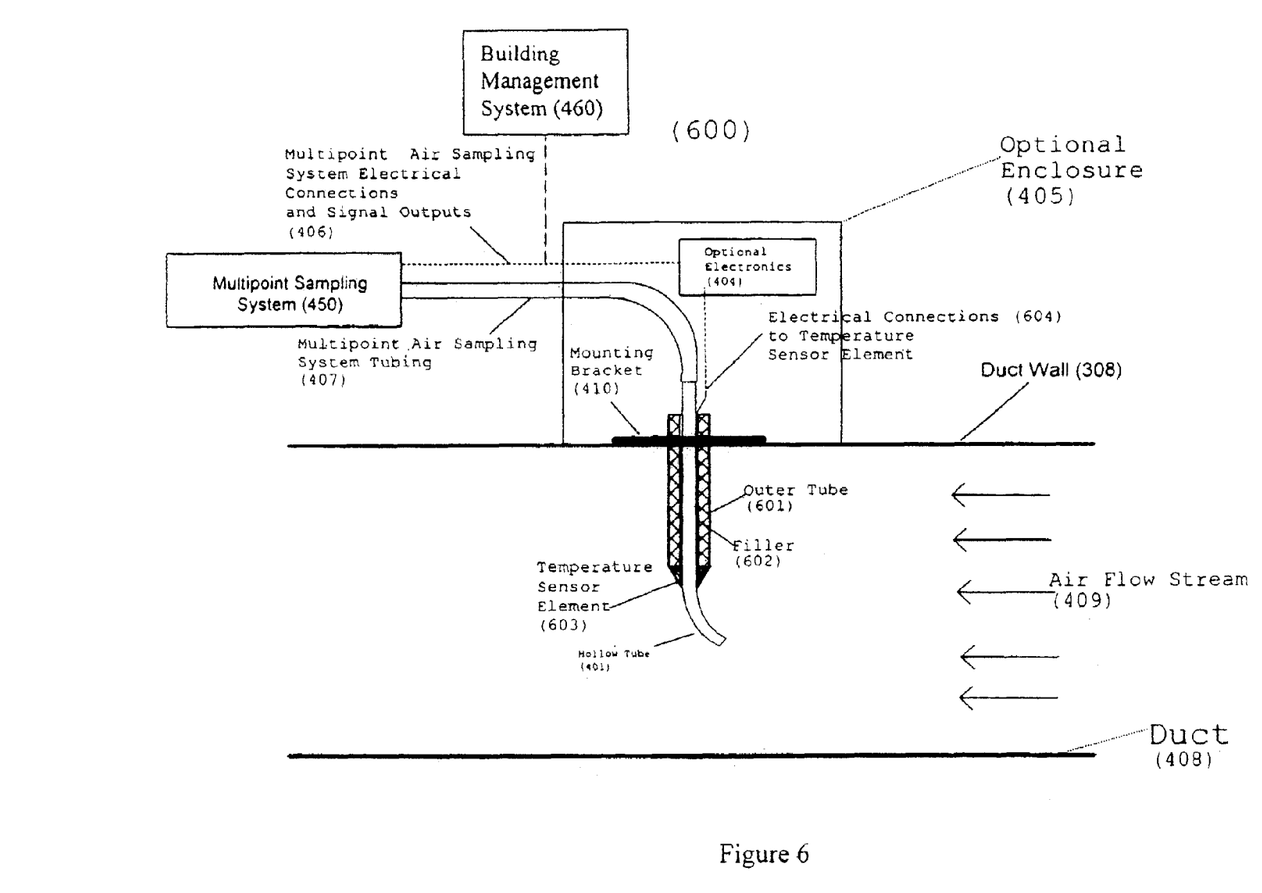
FIG. 6 is a schematic diagram of a preferred embodiment of the invention that combines a sensor probe and an air-sampling probe into one common probe assembly using a hollow thermowell.

Another preferred embodiment is shown in FIG. 6 which integrates an air sampling probe or tube inside of a duct sensor probe such as the duct probe 301 as shown in FIG. 3 to create one common probe assembly using effectively a hollow thermowell approach. Rather than place the temperature sensor in the middle of a thermowell, the middle or a portion of the cross-section of the thermowell is left open or hollow to create a hollow tube 401. This tube 401 has a length that may be as long as the length of the thermowell to allow transport of air from the duct or sensed area coincident with the sensing of some parameter of the air flow stream 409. This results in an outer tube 601, which is made of a thermally conductive material such as a metal like anodized aluminum, which forms the outer diameter of the duct probe 600 and an inner hollow tube 401 that is fixed and located at some point inside the outer tube. This inner tube 401 could be centered in the outer tube or located closer to one side of the outer tube 601.

The connection of the tube 401 to the duct could be from a hole at the end of the thermowell, or the tube may project out of the thermowell as shown in FIG. 6 and be bent into, away from, or perpendicular to the airflow stream 409 as was described for the hollow tube 401 of FIG. 4. Alternatively the hole or connection between the hollow tube 401 and the duct may be only part way down the probe or the thermowell section. For example, the hollow tube 401 could only proceed halfway down the probe length and have a hole in the side of the probe that connects it to the duct interior. In this latter case the end of the outer tube 601 would be sealed as it is with cap 306 in the probe 300 shown in FIG. 3. Having an opening halfway down the probe vs. at the end of the probe could be useful where the duct airflow stream 409 is best sampled at some point other than at the end of the probe, perhaps due to stratification effects in the duct.

The temperature element 603 or some other air parameter-sensing element is then located at a location between the inner tube 401 and the outer tube 601. If it is a temperature sensing element it would be beneficial to also increase the conductivity of the thermal connection between the thermal sensing element 603 and the outer tube 601 using some type of a high thermal conductivity filler 602, For this purpose thermally conductive filler 602 is usually, a two part epoxy that may be metal filled. This filler 602 also maximizes sensor response time and protects the sensor element from moisture.

The temperature-sensing element 603 may be any type of temperature sensing element such as platinum or nickel RTD (in wire or other form), a thermistor, a thermocouple, or a solid-state sensor. Also, element 603 can be a discrete sensor element using only a small portion of the overall length of tube 601, or it can span a large fraction of the entire length of 601, but typically would not exceed the length of 601. A beneficial implementation uses a temperature sensing element that is in wire form that can run up or down the length of the outer tube 601 or beneficially it can be wrapped in a spiral around the inner tube 401 or equivalently around the inside of the outer tube 601 to create an average sensing of the temperature along the entire length of the outer tube 601. The probe can be mounted to the duct through a mounting bracket 410 which can be secured to the duct with one or several sheet metal screws that are driven through mounting bracket 410 into the wall of duct 408 in order to secure the duct probe 600 in place on the duct. To facilitate installation the length of the probe 600 that inserts into the duct may be flexible or bendable so that it can be appropriately positioned for best results.

Additionally, it should be clear to those skilled with air distribution systems that assembly 600 can be applied to ducts of any shape and sizes, the most common shapes being round, rectangular, oval, and square.

Figure 7:
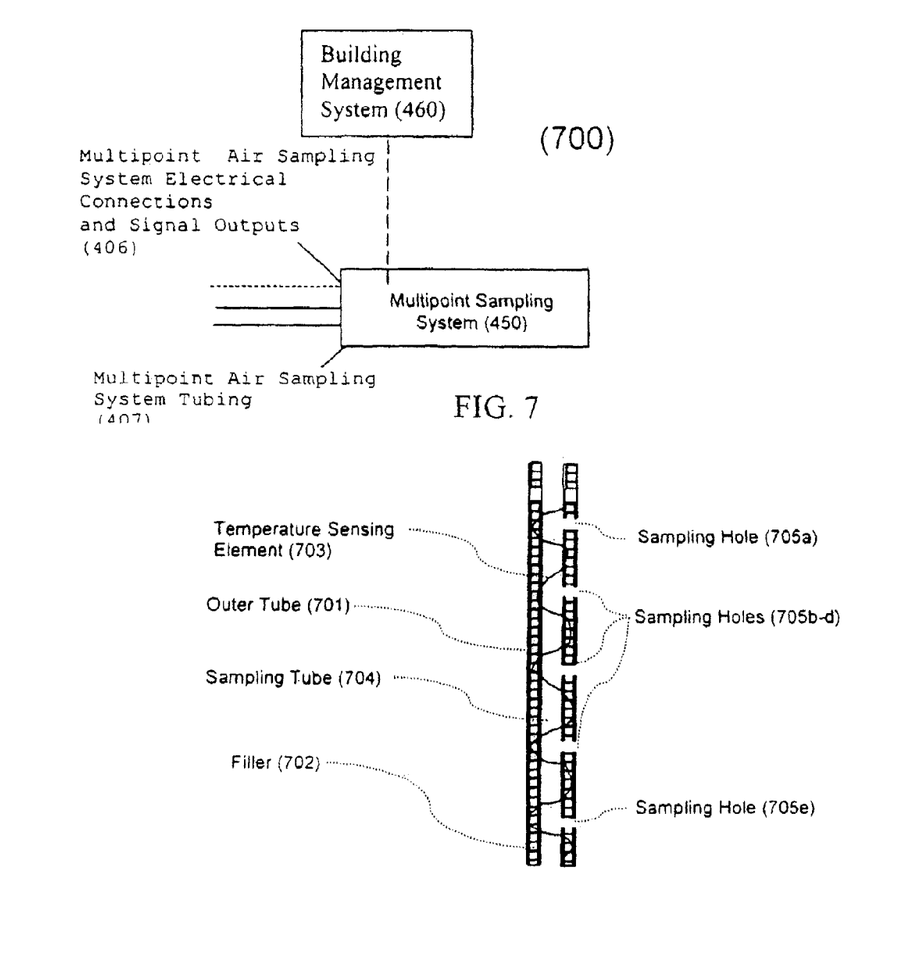
FIG. 7 is a schematic diagram of a preferred embodiment of the invention that combines a temperature or other parameter sensor element into an air-sampling probe that contains multiple sampling holes for sampling multiple areas of a duct.

Another variation of the air sampling duct probe comprises a sampling tube that is perforated with holes along its length to provide a sampling of many areas of the duct vs. just one location to get a better averaging of the gas or particle levels across or though a cross-section of the duct. This is particularly important in the mixed air plenum of an air-handling unit although it can be important in other applications where there is a non-uniform distribution of contaminants in the air across the duct profile. An example of this type of duct probe 700 is shown in FIG. 7 which has the outer tube 701 that traverses much if not all the diameter of the duct 408 and has been perforated with a plurality of sampling holes 705. This duct may be circular, square, rectangular, oval shaped or other duct shapes as may be used by those skilled with air distribution systems.

A plurality of perforated sampling holes 705 are located in the outer tube 704 that allow the air from the airflow stream 409 to enter the sampling tube 704 at multiple locations in the duct or sensed area. These holes of which five happen to be shown in FIG. 7 may directly face the direction of airflow as shown in FIG. 7 or may be placed at a slight angle to the oncoming flow to correct for potential flow velocity mismatches of the flowing air stream vs. the velocity of the sampling air stream. One of the factors behind the position of the sampling holes relates to the concept of isokinetic sampling. As mentioned earlier, isokinetic sampling is achieved if the duct probe or location of the sampling holes is directed into the flowing air stream 409 and the velocity of the air flowing through the sampling tube 704 is matched to the velocity of the air flow stream 409 using one of several techniques well known to those skilled in the art. If instead, the air velocity through the sampling tube 704 is fixed or unrelated to the flowing air stream 409, then the effects of this type of the resultant anisokinetic sampling can generate a higher or potentially lower representation of the concentration of predominately larger sized particles in the air flow stream 409. As a result a preferred embodiment has the air sampling holes located either directly facing the air flow stream 409 for the least effects of anisokinetic sampling, or at a 30 to 45 degree angle to partially compensate for some of the affects of having anisokinetic sampling with a higher relative airflow stream velocity 409.

If it is instead desired to filter out or reduce the number of large sized particles of approximately 5 microns or higher, for example to reduce dust pickup from the sample airflow, the sampling holes should be located at a right angle to the airflow stream 409 or any radial direction beyond 90 degrees to a point completely opposite of the flow direction on the lee side of the probe.

Figure 8:
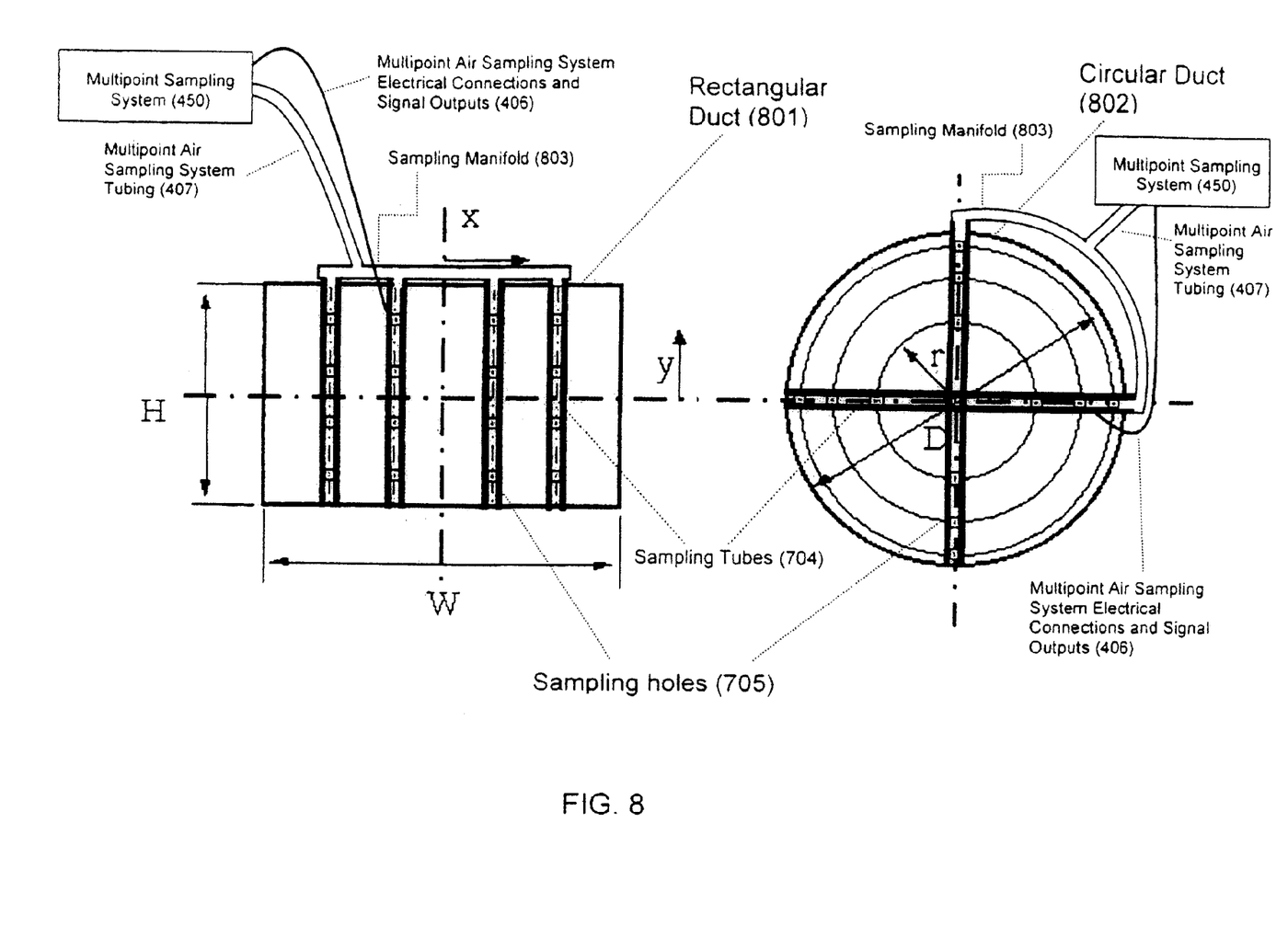
FIG. 8 is a schematic diagram of a preferred embodiment of the invention that combines a temperature or other parameter sensor element into multiple air sampling probes for sensing and sampling multiple areas of a duct in more than one linear dimension.

Generally for larger size ducts such as those over 12 square feet in cross section, rather than use a single probe 704 traversing the duct with a plurality of sampling holes 705 as shown in FIG. 7, another embodiment may be employed such as that shown in FIG. 8, using an array of sampling tubes 704 to traverse a duct of any cross sectional shape at different locations perpendicular to the length of the duct. FIG. 8 shows both a rectangular array for rectangular duct 801 as well as a radial array for a circular duct 802. Other similar shaped arrays can also be used for other shaped ducts such as square, oval etc. Similarly more or less sampling tubes can be employed than shown in FIG. 8 based on the size of the duct. Using multiple sampling probes yields an even better averaging of the contaminant distribution in a duct by incorporating measurements in two dimensions vs just one linear dimension. The various sampling tubes 704 employed within the plurality of sampling probes are connected together by a manifold 803 of some type such as a piece of tubing with an inner diameter at least as large, and preferably larger than inner diameter of the sampling tubes 704 to minimize the pressure drop across the manifold. The manifold can be located outside the duct as shown in FIG. 8 to simplify installation and improve serviceability or located inside the ductwork to reduce the number of duct penetrations. For the sampling tubes 704 in circular duct 802, the sampling tubes can be connected in the center where the sampling tubes 704 cross such that a manifold 803 is not required in this implementation. By interconnecting these sampling tubes the contaminants or airflow parameters that are being measured from all of the sampling holes are collected to get a better average measurement of the air in the duct.

In addition to using a thermowell and a temperature sensing element in the duct probe, other sensing approaches may also be employed. For example, discrete sensing elements such as thermistors for temperature, solid state humidity sensing elements for humidity, or any other discrete sensor element may be located next to each of the sampling holes 705 in FIGS. 7 and 8 to provide a plurality of measurements that can be averaged to get a good average measurement of the duct conditions. Where thermistors or RTD's (resistance temperature detectors) are used for temperature for example these sensors can be connected in either a series format or even in a parallel format to provide a total average resistance. This resistance can then be easily measured using conventional thermistor/RTD sensing electronics and converted into a temperature signal output to provide a good measurement of the average duct temperature.

The spacing of the sampling holes 705 and the sensor element locations 703 where discrete sensors are used along the length of the probes in both FIGS. 7 and 8 may be uniform and evenly distributed or may be specially spaced to take into account the varying areas of the duct sensed at different locations in a duct. For example, in sampling a round duct with a sampling tube that cuts across the diameter of the duct from one side to the other side, a hole near the outside of the duct would be representative of a larger ring of area vs a hole near the center of the duct which would be representative of a smaller ring of area. Thus to get holes that are sampling roughly equal areas of the duct to get a true average, the hole in the sampling tube near the outside of the duct should be closer together and greater in number than holes in the sampling tube that are near the center of the duct. This concept is similar to that used when measuring total air flow in a duct using a survey technique that employs pitot static tubes or point air velocity measurement instruments to measure air velocities in a duct at certain locations that allow a better average airflow measurement using cross-sectional areas of similar size. The survey is typically performed with the grid of locations shown in FIG. 8 and the following Table 1 excerpted from a reference article from Flow Kinetics LLC. As shown, either the Centroids of Equal Areas or Log-Tchebycheff point distribution may be used for example with this technique. Similarly we can use these same locations as the locations of the sampling holes 705 and or sensor element 703 locations in the duct probe or probes. When these locations are used a better, more accurate average of the duct conditions will result.

TABLE 1

Traverse point for rectangular and circular ducts. Either Centroids of Equal Areas or Log-Tchebycheff point distributions can be used.

Rectangular ducts - Centroids of Equal Areas

| Rows or Points/Row | Distance from Center-line, x/W or y/H | | | |
|---|---|---|---|---|
| 4 | ±0.125 | ±0.375 | | |
| 5 | 0 | ±0.2 | ±0.4 | |
| 6 | ±0.083 | ±0.25 | ±0.417 | |
| 7 | 0 | ±0.143 | ±0.286 | ±0.429 |

Circular ducts - Centroids of Equal Areas

| Points/Radius | Distance from Center, r/D | | | | |
|---|---|---|---|---|---|
| 3 | 0.204 | 0.353 | 0.457 | | |
| 4 | 0.177 | 0.306 | 0.395 | 0.468 | |
| 5 | 0.158 | 0.274 | 0.354 | 0.418 | 0.474 |
| 6 | 0.144 | 0.25 | 0.323 | 0.382 | 0.433 | 0.479 |

Rectangular ducts - Log-Tchebycheff

| Rows or Points/Row | Distance from Center-line, x/W or y/H | | | |
|---|---|---|---|---|
| 5 | 0 | ±0.212 | ±0.426 | |
| 6 | ±0.063 | ±0.265 | ±0.439 | |
| 7 | 0 | ±0.134 | ±0.297 | ±0.447 |

Circular ducts - Log-Tchebycheff

| Points/Radius | Distance from Center, r/D | | | | |
|---|---|---|---|---|---|
| 3 | 0.188 | 0.362 | 0.468 | | |
| 4 | 0.166 | 0.306 | 0.4 | 0.476 | |
| 5 | 0.143 | 0.295 | 0.345 | 0.424 | 0.481 |

It should be further noted that this equal areas technique assumes that the flow rates through each sampling hole 705 will be similar. To ensure that this assumption will be true with equal sized sampling holes 705, it is important that the pressure drop across the sampling holes 705 is large in reference to the pressure drop along the length of the inside of the sampling tube 704 from the sampling hole 705a closest to the beginning of the sampling tube 704 to the sampling hole 705e farthest away. To a first order the difference in flow through the first hole vs. the last hole will be equal to the square root of the ratio of the pressure drop across the last hole and the pressure drop along the length of the sampling tube vs. the pressure drop of the first hole, assuming pressure drops that are representative of equal flow rates through each hole. Thus in a preferred embodiment to get a flow variation equal to 5% or less between the first sampling hole and the last sampling hole the preceding equation indicates that the sampling tube 704 pressure drop between sampling holes 705a and 705e should be no more than 10% of the pressure drops through the sampling holes 705. One way to increase this favorable pressure drop variation is to decrease the size of the holes 705 relative to the diameter of the sampling tube 704. For example, for a preferred inner diameter of the sampling tube 704 of approximately 0.25 inches ID, and assuming a sampling tube length of one foot and the use of 5 sampling holes located in the sampling tube 704 as shown in FIG. 7, a representative sampling hole 705 diameter of about 0.025 inches will create a flow uniformity of approximately 5% between the 5 sampling holes 705.

Another approach for creating equal flows through the sampling holes with less pressure drop across the holes is to vary the size of the holes such that the closest hole to the beginning of the sampling tube such as sampling hole 705a in FIG. 7 is smallest and the sampling hole 705e diameter would be largest. The calculation of these sampling hole sizes is similar to that used by engineers skilled in the art of sizing HVAC ductwork for equal percentage drop whereby the pressure drop from the beginning of the sampling tube 704 to the exterior of the sampling holes 705 will be designed to be the same for each hole.

Figure 9:
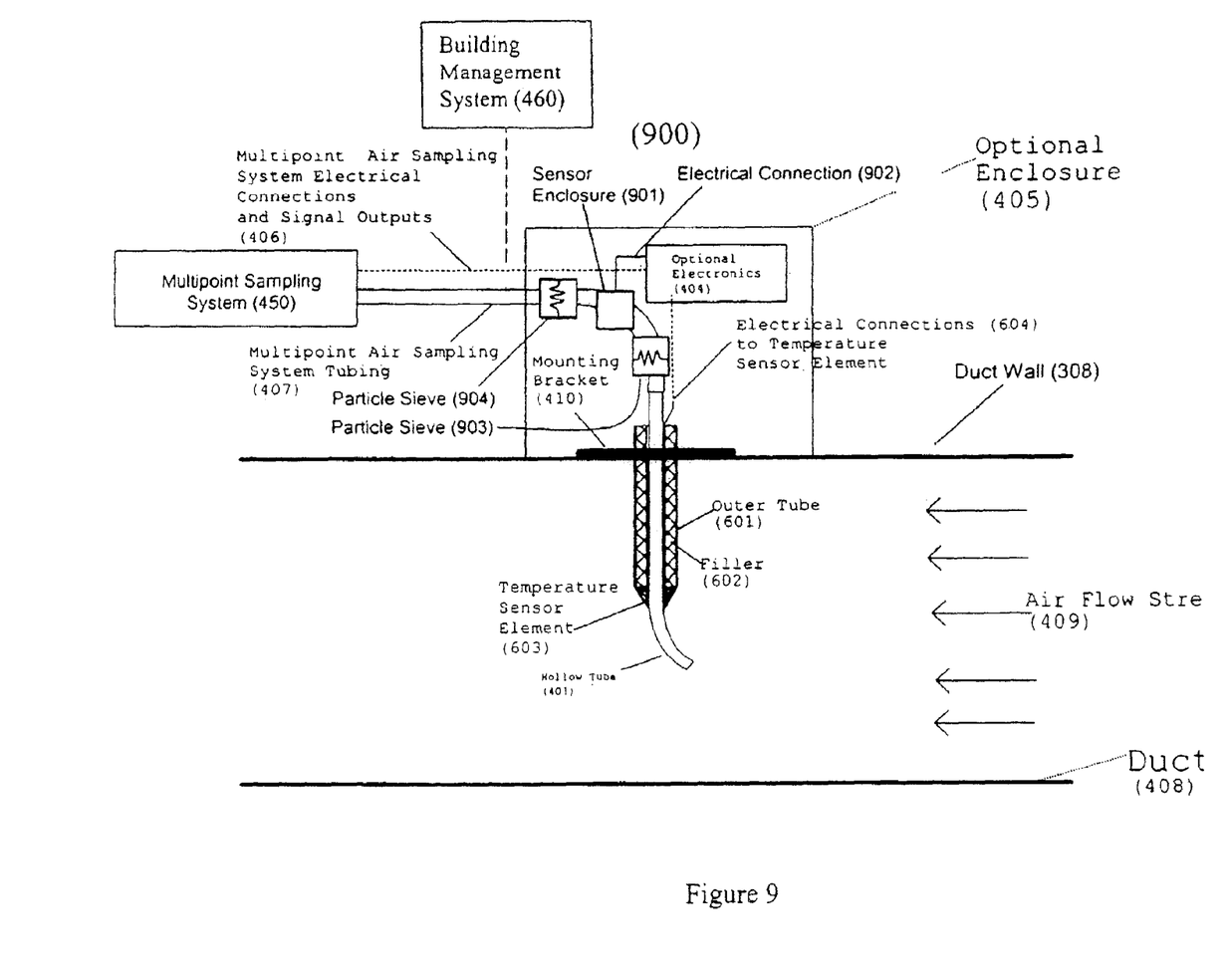
FIG. 9 is a schematic diagram of a preferred embodiment of the invention that combines a sensor probe and an air-sampling probe into one common probe assembly in addition to including additional sensors and or particle sieves.

In another embodiment, shown in FIG. 9, the probe assembly 900 includes a sensor chamber 901 that connects to hollow tube 401 and multipoint air sampling tubing 407 in such a way that it enables any number of sensors disposed within 901 to be exposed to the air sample drawn through hollow tube 401 by the multipoint sampling system 450. Sensor chamber 901 may contain sensor elements with or without signal conditioning circuitry and such sensors with optional circuitry may connect to optional electronics 404, via electrical connection 902 in order to have access to multipoint air sampling system electrical connections 406, or sensor chamber 901 may connect directly to 406. Sensor chamber 901 is constructed in such a way that it provides a gas tight connection to hollow tube 401 and multipoint air sampling tubing 407 and exposes the sensors that are housed within 901 to the sampled air stream drawn by multipoint sampling system 450 through hollow tube 401. The configuration shown in 900 is advantageous when sampling one or a number of parameters from air flow stream 409, such as ozone or large particles for example, that may not transport well within tubing 407 that additionally requires sensors that either are too big to attach to a portion of hollow tube 401 that penetrates duct 408, or that should not be directly exposed to air stream 409. In addition, locating such sensors within sensor chamber 901, enables such sensors to be replaced or serviced without having to remove the hollow tube 401 and related assembly.

Additionally, FIG. 9 also shows the addition of particle sieves 903 or 904 to the enclosure 405. A particle sieve is another name for a screen or filter element that is designed to filter out large particles but typically, although not always, is designed to pass small particles that are to be sensed by the centralized sensors. This is important where the air flow stream that is being sensed may contain a lot of dust, particulates, human or animal hair, carpet or other fibers, bed lint, etc that is useful to screen out so as not to allow these materials to enter the air sampling system where they may contaminant the system. Where not even small particles are desired to be sensed the particle sieve may be a high grade air filter such as a HEPA filter that filters out a very high percentage of fibers, large particles and even small particles. Any type of filter with an industry MERV rating of 16 or above for example will be sufficient where almost complete filtration of all size particles is desired.

Where small particles are desired to be sensed by centralized sensors, a particle sieve that passes small particles is desired. An example of a particle sieve that can pass small particles is a screen element with holes that are large enough to pass the small particles of interest but small enough to block larger particles, fibers or hair. An example of a particle sieve that can pass small particles would be a wire screen with holes that are between 2 and 20 thousands of an inch in diameter. To create more surface area to prevent the screen from becoming blocked by larger particles in a short period of time, the total surface area of the screen or sieve can be enlarged by using a pleated structure using folds or waves of screen material as shown by particles sieve 903 or 904 in FIG. 9.

When the sensor chamber 901 does not contain a particle sensor of a type that measures larger size particles, fibers, or hair such as those larger than 10 microns in diameter, it would probably be advantageous to filter the air before the sensor chamber as shown by the particle sieve 903 that is located before the sensor enclosure 901 in FIG. 9. In this case particle sieve 904 would most likely not be required. If the sensor chamber 901 does however contain a particle counter or other sensor that measures or needs to detect or measure particles, fibers or hair in the air larger than about 10 microns in diameter, then it would be advantageous to use particle sieve 904 and not use particle sieve 903.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A probe assembly system for extracting an air sample from a flowing air stream located inside of a building's air handling unit and providing the air sample to a multipoint sampling system through a system tube, comprising:
   a sampling tube which is at least partially immersed in said flowing air stream and is adapted to enable said air sample to pass through the sampling tube to the system tube;
   at least one sensor assembly mounted to the sampling tube and at least partially located in the building's air handling unit that is adapted to sense one or more characteristics of said flowing air stream and generate a signal representative of the one or more sensed characteristics, where the signal is communicated to the multipoint air sampling system; and
   a sensor chamber connected to the sampling tube and to the system tube that is adapted to enable at least a second sensor assembly disposed within the sensor chamber to be exposed to the air sample to sense one more characteristics of the flowing air stream.

2. The probe assembly system of claim 1, wherein the sampling tube extracts said air sample isokinetically.

3. The probe assembly system of claim 1, wherein said sampling tube is adapted to extract said air sample to compensate for any effects of an anisokinetic sampling of the flowing air stream.

4. The probe assembly system of claim 1, wherein the at least one sensor assembly comprises an ozone sensor.

5. The probe assembly system of claim 1, wherein the at least one sensor assembly comprises a humidity sensor.

6. The probe assembly system of claim 1, wherein said flowing air stream is located inside a mixed air plenum of said building's air handling unit.

7. The probe assembly system of claim 1, wherein said flowing air stream is located inside a portion of a duct system of said building's heating, ventilating and air conditioning (HVAC) system.

8. The probe assembly system of claim 1, wherein the at least one sensor assembly comprises a particle counter.

9. The probe assembly system of claim 1, wherein the at least one sensor assembly comprises a volatile organic compound (VOC) sensor.

10. The probe assembly system of claim 1, wherein said sampling tube is perforated with a plurality of sampling holes, and wherein said sampling tube samples said flowing air stream through the plurality of sampling holes.

11. The probe assembly system of claim 10, wherein said sampling holes in said sampling tube are located at positions along at least a portion of a length of said sampling tube, and wherein said sampling holes are positioned such that the velocity of the air sample flowing through at least one of said sampling holes is approximately equal to the velocity of the flowing air stream.

12. The probe assembly of claim 10, wherein the at least one sensor assembly comprises at least one sensor element that is located in close proximity to at least two of said sampling holes.

13. The probe assembly system of claim 1, wherein the at least one of sensor assembly generates a signal that is in direct communication with a building management system.

14. The probe assembly system of claim 1, further comprising a probe housing, wherein the at least one sensor assembly is in direct communication with a signal conditioning circuit that is located within said probe housing, and said signal conditioning circuit is in direct communication with a building management system.

15. The probe assembly system of claim 1, further comprising a particle sieve that is adapted to at least partially filter said air sample.

16. The probe assembly system of claim 1, wherein the at least one sensor assembly comprises a particle sensor.

17. The probe assembly system of claim 1, wherein the at least one sensor assembly comprises an ozone sensor.

18. A method of using a probe assembly for extracting an air sample from a flowing air stream located inside a building's air handling unit and providing the air sample to a multipoint sampling system through a system tube, comprising the steps of:

provided a probe assembly comprising, a sampling tube, which is at least partially immersed in said flowing air stream, through which said air sample passes and is transferred to the system tube;

at least one sensor assembly mounted to the sampling tube and at least partially located in the building's air handling unit that is adapted to sense at least one characteristic of said flowing air stream and generate a signal representative of the one or more sensed characteristics, where the signal is communicated to the multipoint sampling system; and a sensor chamber connected to the sampling tube and to the system tube that is adapted to enable at least a second sensor assembly disposed within the sensor chamber to be exposed to the air sample to sense one or more characteristics of the flowing air stream; and using the probe assembly to sense at least one characteristic of said flowing air stream.

19. The method of claim 18, wherein said sampling tube extracts said air sample isokinetically.

20. The method of claim 18, wherein said sampling tube extracts said air sample to at least partially compensate for any effects of an anisokinetic sampling of the flowing air steam.

21. The method of claim 18, wherein said flowing air stream is located inside a mixed air plenum of said building's air handling unit.

22. The method of claim 18, wherein said flowing air stream is located inside a portion of a duct system of said building's heating, ventilating and air conditioning (HVAC) system.

23. The method of claim 18, wherein said sampling tube is perforated with a plurality of sampling holes, and wherein said sampling tube samples said flowing air stream through the plurality of sampling holes.

24. The method of claim 23, wherein said sampling holes in said sampling tube are located at positions along at least a portion of said sampling tube, and wherein said sampling holes are positioned such that the velocity of the air sample flowing through at least one of said sampling holes is approximately equal to the velocity of the flowing air stream.

25. The method of claim 18, wherein said probe assembly further comprises a plurality of sampling tubes wherein each of said sampling tubes is perforated with at least one sampling hole that is adapted to sample said flowing air stream and wherein the at least one sensor assembly comprises sensor elements that are located in close proximity to at least two of said sampling holes.

26. The method of claim 18, wherein the at least one sensor assembly generates a signal that is in direct communication with a building management system.

27. The method of claim 18, wherein the at least one sensor assembly is in direct communication with a signal conditioning circuit that is housed within said probe assembly, and wherein said signal conditioning circuit is in direct communication with a building management system.

28. The method of claim 18 further comprising a particle sieve that is adapted to at least partially filter said air sample.

29. The method of claim 28 wherein the particle sieve is located proximate said probe assembly.

* * * * *